(12) United States Patent
Lilischkis et al.

(10) Patent No.: US 7,029,615 B2
(45) Date of Patent: Apr. 18, 2006

(54) METHOD FOR PRODUCTION OF MATERIAL BLOCKS WITH MULTIPLE TEST SAMPLES

(75) Inventors: Richard Lilischkis, Hannover (DE); Reinhard Wasielewski, Hannover (DE); Michael Mengel, Brombergerstr. 17, Hannover D-30659 (DE)

(73) Assignees: Reinhard Von Wasielewski, Hannover (DE); Michael Mengel, Hannover (DE)

( * ) Notice: Subject to any disclaimer, the term of this patent is extended or adjusted under 35 U.S.C. 154(b) by 409 days.

(21) Appl. No.: 10/169,960

(22) PCT Filed: Dec. 22, 2000

(86) PCT No.: PCT/DE00/04647

§ 371 (c)(1),
(2), (4) Date: Aug. 13, 2002

(87) PCT Pub. No.: WO01/51910

PCT Pub. Date: Jul. 19, 2001

(65) Prior Publication Data

US 2003/0038401 A1 Feb. 27, 2003

(30) Foreign Application Priority Data

Jan. 13, 2000 (DE) .................. 100 01 136

(51) Int. Cl.
*B29C 65/00* (2006.01)

(52) U.S. Cl. ....................... 264/248; 264/299

(58) Field of Classification Search ................ 264/155, 264/219, 248, 299, 319; 435/401, 40.5, 40.52, 435/287.2
See application file for complete search history.

(56) References Cited

U.S. PATENT DOCUMENTS

| | | | |
|---|---|---|---|
| 4,272,049 A | 6/1981 | Kindel | 249/83 |
| 4,443,395 A | 4/1984 | Motta | 264/117 |
| 4,820,504 A | 4/1989 | Battifora | 424/3 |
| 4,914,022 A | 4/1990 | Furmanski et al. | 435/7 |
| 5,002,377 A | 3/1991 | Battifora et al. | 350/535 |
| 6,101,946 A * | 8/2000 | Martinsky | 101/494 |
| 6,103,518 A * | 8/2000 | Leighton | 435/286.3 |

FOREIGN PATENT DOCUMENTS

| | | |
|---|---|---|
| EP | 0138351 A2 | 4/1985 |
| EP | 0139424 A2 | 5/1985 |
| EP | 0142574 A1 | 5/1985 |
| FR | 2502539 | 10/1982 |
| FR | 2667938 A1 | 4/1992 |
| GB | 2046940 A | 11/1980 |
| GB | 2144366 A | 3/1985 |
| WO | WO 99/13313 | 3/1999 |
| WO | WO 99/19711 | 4/1999 |
| WO | WO 99/44062 | 9/1999 |

OTHER PUBLICATIONS

Battifora et al. 1990.Laboratory Investigation, vol. 63, pp. 722-724.*
Battifora "The Multitumor (Sausage) Tissue Block: Novel Method for Immunohistochemical Antibody Testing", Laboratory Investigation, vol. 55, No. 2, 1986, pp. 244-248.
Battifora and Mehta "The Checkerboard Tissue Block. An Imporved Multitissue Control Block", Laboratory Investigation, vol. 63, No. 5, 1990, pp. 722-724.
Kononen et al. "Tissue Microarrays for High-Throughput Molecular Profiling of Tumor Specimens", Nature Medicine, vol. 4, No. 7, Jul. 1998, pp. 844-847.

* cited by examiner

*Primary Examiner*—Ralph Gitomer
*Assistant Examiner*—Kailash C. Srivastava

(57) ABSTRACT

In a method for the production of a material block containing a number of test samples, particularly tissue samples, a material blank, preferably made of paraffin and containing a number of openings to accommodate the corresponding tissue samples, is first produced, whereby a material blank is formed with a regular arrangement of openings by means of a suitably shaped casting mold, with said openings extending from the first main surface of the material blank in the direction of a second main surface of the material blank up to a specific depth, preferably penetrating completely through the block. These openings are then filled with tissue samples in the form of cylindrical tissue cores, and these cores are closely bonded with the surrounding material of the material blank, preferably by means of a double-melt procedure.

17 Claims, 6 Drawing Sheets

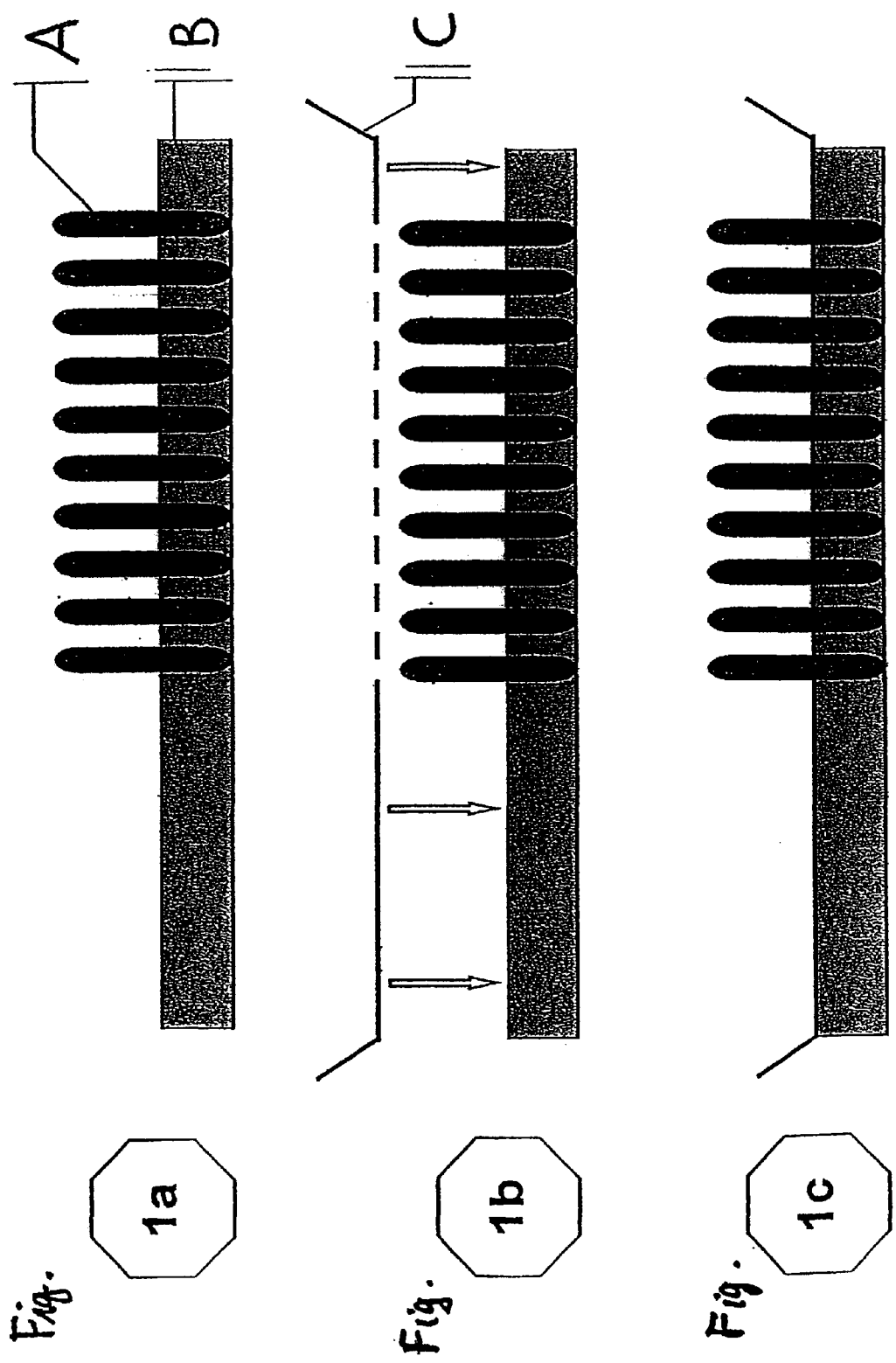

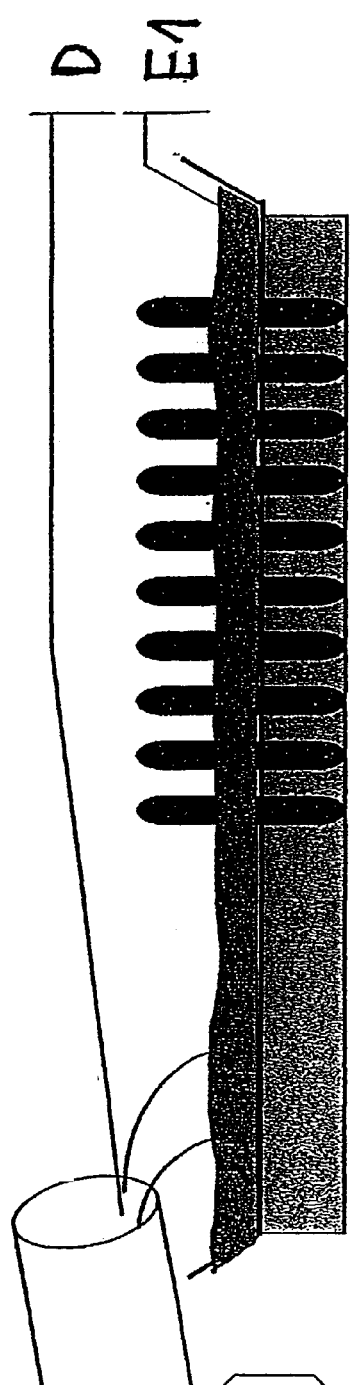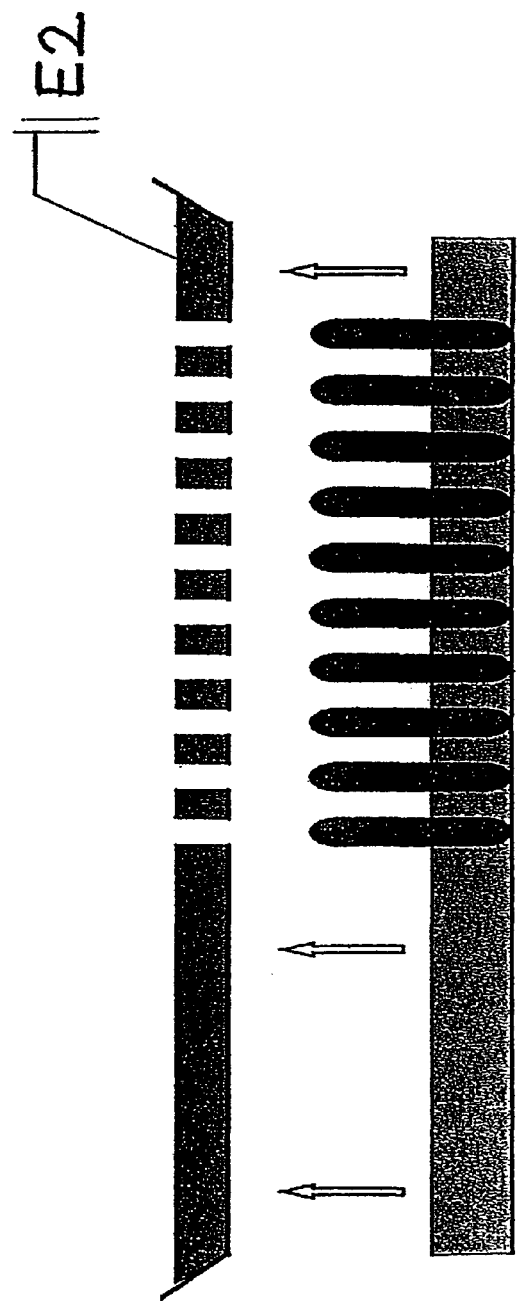

Figures 5A, 5B, 5C:
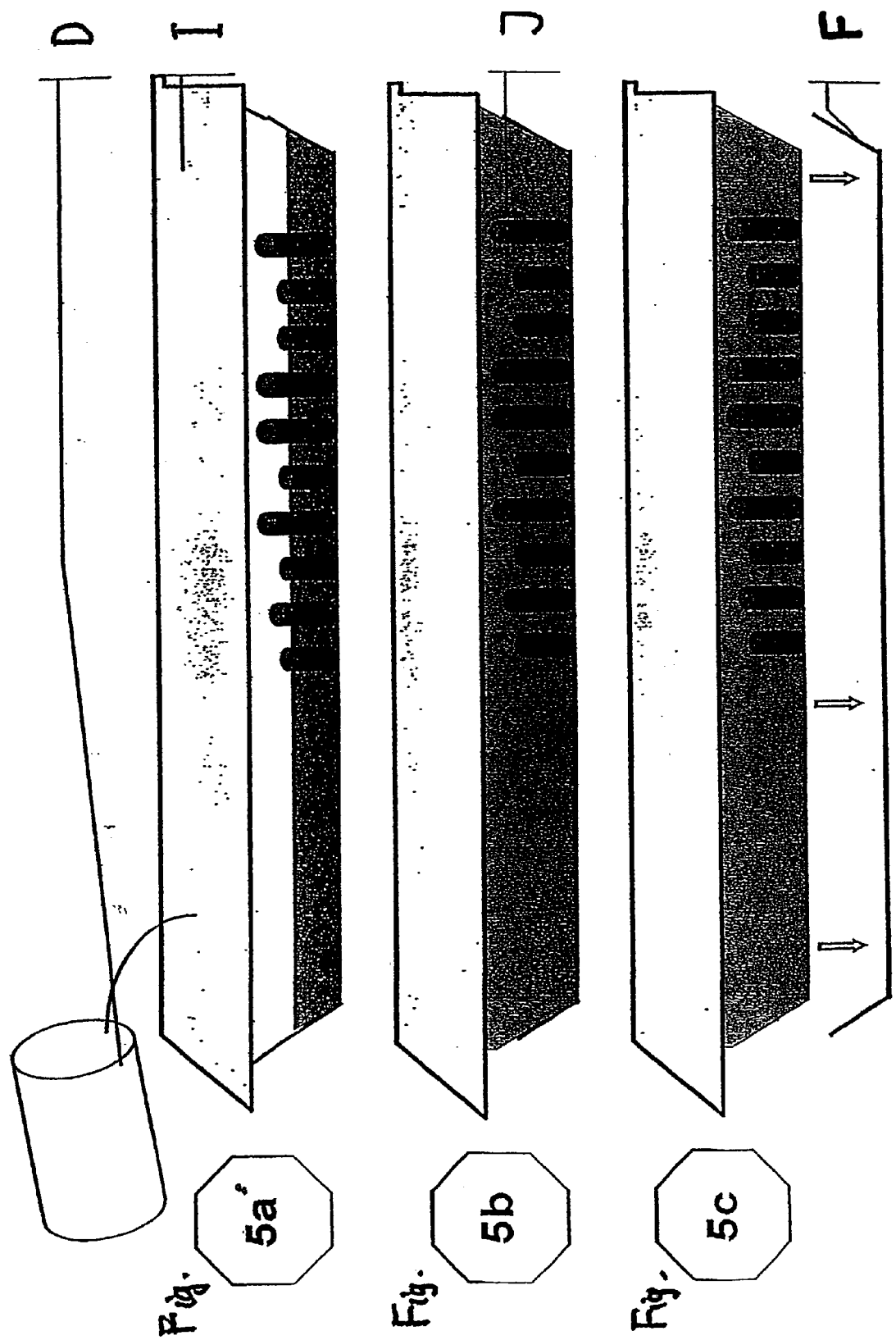

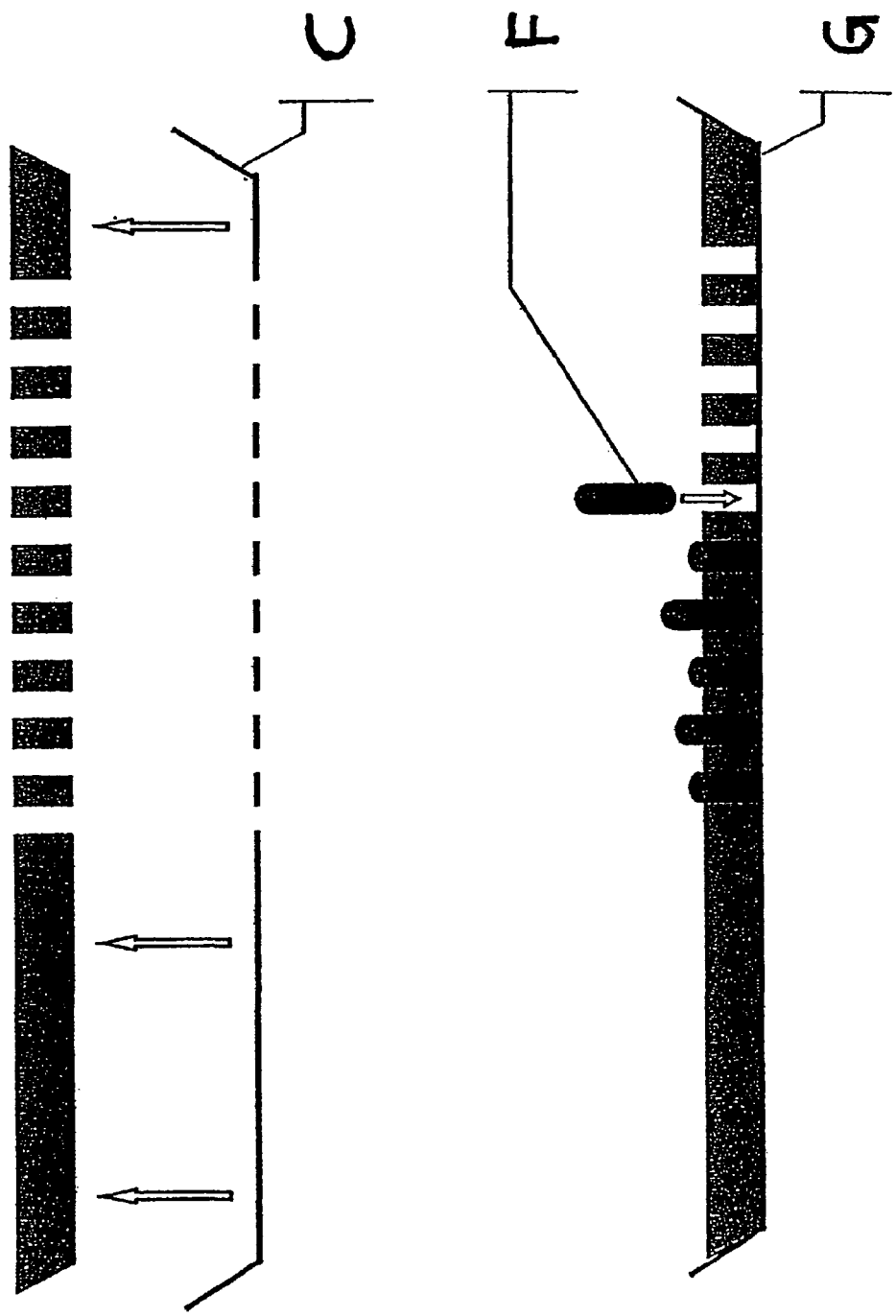
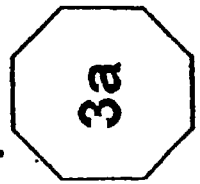
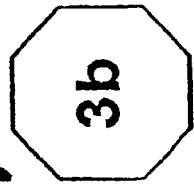

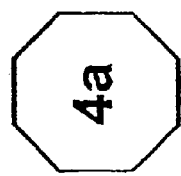
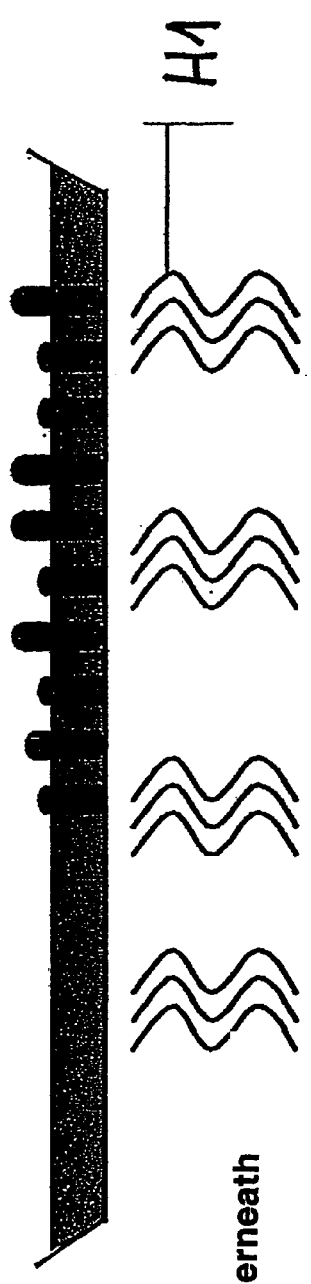
A = From Underneath
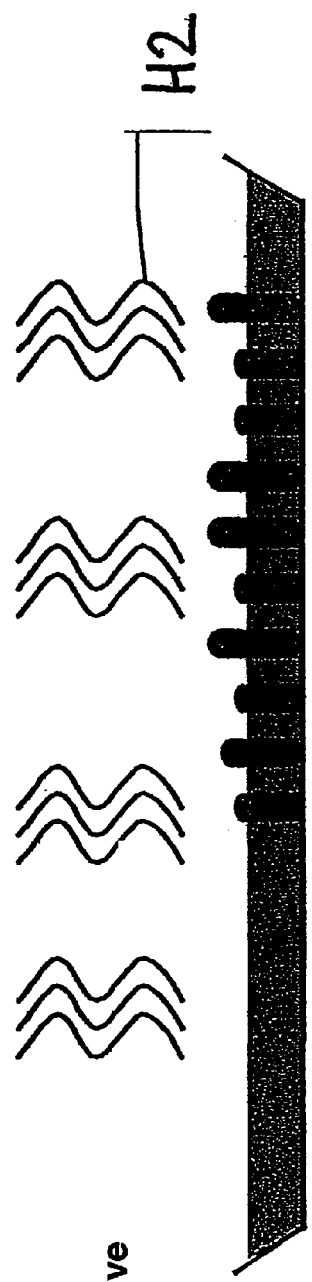
B = From Above

METHOD FOR PRODUCTION OF MATERIAL BLOCKS WITH MULTIPLE TEST SAMPLES

The invention concerns a method for the production of a material blank containing a number of openings to accommodate tissue test samples according to the features of claim 1, a method for the production of a material block containing a number of tissue test samples according to the features of claim 2, a method for the production of thin sample sections containing a number of test samples according to the features of claim 3, and a material blank with a regular arrangement of openings to accommodate test samples according to the features of claim 14.

The present invention relates to the field of testing or processing human, animal, or plant tissue samples, as well as microorganisms, cell cultures, or matrix macromolecules, using methods that are known in the state of the art, such as histological or immunohistochemical testing techniques. Various methods have been developed in the state of the art to produce tissue sections with multiple tissue samples, allowing these tests to be performed simultaneously and thus a large quantity of samples to be tested within a reasonable time. The simultaneous testing of multiple tissue samples in one tissue section offers many advantages. In addition to significant savings in costs and time, simultaneous testing using the various testing techniques such as histology, histochemistry, immunohistochemistry, and in situ hybridization also ensures that all of the simultaneously tested samples are tested under identical laboratory and testing conditions, which permits quality control and quality assurance in the test results. The present method for the production of multi-blocks was designed to fulfill the following prerequisites:

1. Once the tissue samples have been embedded, it must be possible to orient the individual samples, i.e. assign them to their source (which sample belongs to which patient).
2. The tissue block should be suitable for all routine tissue processing methods (various staining techniques), and should not require any separate and/or specific additional processing after production (e.g. special cutting technique).
3. It should be possible to use the method with minimal effort, in a short amount of time, and without high costs.
4. The tissue and section quality of the multi-block should be identical to that of standard blocks, which are usually made of paraffin.
5. The tissue samples should have a representative sample size in order to ensure reliable analysis.
6. The tissue samples should be suitable for long-term archiving.

A number of methods for the production of paraffin blocks with multiple tissue samples have already been described in the state of the art, and each of these methods offers various advantages and disadvantages. None of the many methods, however, permits the production of a paraffin block with multiple tissue samples, which can then be further processed without limitations in the same manner as a typical standard paraffin block, and which can at the same time be produced simply, cost-effectively, and with minimal time expenditure.

U.S. Pat. Nos. 4,820,504 and 5,002,377 describe methods in which the starting tissue must first be deparaffinized in order to be reembedded in paraffin later in the form of rod-shaped pieces of tissue. This method is both time-consuming and laborious. In addition, typical archived material generally cannot be used for this purpose, since many archived tissue samples are too small, which usually makes it impossible to obtain rod-shaped pieces of tissue from this material. In addition, the laboriously prepared rod-shaped pieces of tissue must first be transferred into a fragile medium (agar) prior to being reembedded in paraffin. This requires placing them in specially-prepared containers (moles), so that they can subsequently be embedded in an oriented manner in the tissue block with multiple tissue samples.

U.S. Pat. No. 4,914,022 describes a method in which cylindrical tissue cores are obtained from archived standard paraffin blocks by means of a core needle, with the cores then being embedded in a new paraffin block with a placeholder (straw). This method, however, offers only a limited orientation of the multiple cylindrical tissue cores, because a number of cylindrical tissue cores (24 or more) can be embedded together in one placeholder.

Kononen et al., in "Nature Medicine 4:844–847," 1998, also describe the production of paraffin blocks with multiple tissue samples using a technically complex device, which also obtains cylindrical tissue cores from archived standard paraffin blocks by means of a core needle. If very thin needles are used, the device permits the production of tissue blocks with a large quantity of tissue samples (up to 1,000), which can be placed in the tissue block in an oriented manner. Nevertheless, the method has a number of disadvantages:

the acquisition costs of the device are very high,
the simultaneous production of a number of tissue blocks with multiple tissue samples (commercial use as a service) requires using a number of the devices,
the large quantity of very small (500–600 µm in diameter) samples produced with this device requires a very precise and thus very time-intensive use of the device. Also, the size of the tissue available for analysis is very small, which limits its suitability for evaluation.
the extremely thin cylindrical tissue cores are fragile and therefore cannot be practically archived.
The obtained cores must be placed into special, soft paraffin. The produced paraffin block with multiple tissue samples can then be cut or further processed only by using a special film. This film must be placed on the block before each tissue section is cut to prevent the paraffin section from "dispersing" on the water bath. In addition, suitably thin section preparations (8 µm instead of the normal 2–5 µm) cannot be produced with this method, which can significantly limit the ability to evaluate various staining results.

The aim of the present invention is therefore to specify a method for the production of a material block containing a number of test samples, particularly tissue samples, by means of which method such a material block can be produced with minimal effort and within a relatively short time. At the same time, it should be possible to orient or assign the individual embedded tissue samples to their source. The quality of the material block should be such that it is suitable for all routine tissue processing methods, does not require any separate and/or specific additional processing after production, and the quality of the tissue and sections from the material block is identical to that of standard paraffin blocks. The tissue samples embedded in the material block should also be of a representative sample size in order to ensure reliable analysis, and should be suitable for long-term archiving.

These aims have been achieved through the features of the independent patent claims. According to these claims, the invention describes a method for the production of a material blank containing a number of openings to accommodate test samples, in which a material blank with a regular arrangement of openings is formed using an appropriately shaped casting mold, whereby said openings extend from an initial main surface of the material blank in the direction of a second main surface of the material blank to a specific depth.

The invention further describes a method for the production of a material block containing a number of test samples, in which
a) a material blank is produced as described above, and
b) test samples are placed in at least some of the available openings in the material blank and are firmly bonded with the surrounding material of the material blank.

The invention further describes a method for the production of thin sample sections containing a number of test samples in which, following production of a material block as described above, sample sections are cut off from one of its main surfaces, on which the test samples inserted into the material block are exposed.

Finally, the invention relates to a material blank with a regular arrangement of openings to accommodate test samples, whereby said openings extend from an initial main surface of the material blank in the direction of a second main surface of the material blank.

In an embodiment of the invention described in detail below, paraffin is used as the material for the material blank. In this embodiment, the openings created in the material blank are in the form of openings that penetrate completely through the block.

The invention therefore comprises in particular a new, optimized method for the production of material blocks with multiple tissue samples (multi-blocks). This method offers all of the advantages of previously known methods, and also avoids their disadvantages, thus producing as an end product a multi-block that can be further processed in the same manner as a standard paraffin block.

The method presented here is preferably based on the production of cylindrical tissue cores, which can be punched out with a core needle from tissue samples embedded in typical paraffin. These cylindrical tissue cores are then embedded in an oriented manner in a so-called "paraffin blank" manufactured using the appropriate casting mold. Preferably a double-melt procedure is then applied to a paraffin blank with multiple cylindrical tissue cores to create a homogeneous, stable multi-block, which can be normally cut and processed with all current methods.

Particularly noteworthy advantages of the method according to the invention are:
1. Large, conventional archives of standard paraffin blocks, e.g. in anatomical or pathological institutions, can be used to obtain the cylindrical tissue cores. Relatively small archived tissue samples can also be used as starting tissue. Deparaffinizing and subsequent reembedding of the obtained tissue is not necessary, nor is it necessary to temporarily embed the tissue in agar. The cylindrical tissue cores can be obtained with any type of core needle (e.g. typical medical tissue biopsy needles). The diameter of the core needle, and thus of the cylindrical tissue core and the tissue sample to be evaluated, can therefore be varied as desired. The cylindrical tissue core can be obtained in any location without extensive prior knowledge and with minimal technical effort. Cylindrical tissue cores from tissue areas that are of interest can be obtained from the archived blocks by means of prior microscopic inspection of a conventional (hematoxylineosine) stained tissue section. The cylindrical tissue cores thus obtained can themselves be easily and securely archived.
2. The material blank produced using the casting mold permits the exact orienting embedding of the cylindrical tissue cores. Preferably the material blank consists of homogeneous paraffin and does not contain any foreign material as a placeholder, as this could impair further processing of the block. The blank can also be produced easily, cost-effectively, and quickly. It can be shipped to any location, filled there with cylindrical tissue cores of the appropriate diameter, and then finished as a multi-block by means of the double-melt procedure. In this way, a multi-block can be produced with no additional technical equipment other than a commercially available pincette to facilitate the insertion of the cylindrical tissue cores into the material blank.
3. An arrangement described for the first time for the simple, cost-effective, and rapid production of material blanks is used as a casting mold. This casting mold is the basis for the subsequently decisive orienting embedding of the multiple cylindrical tissue cores. It allows the material blank to be produced in a manner that is chronologically and spatially independent from the production of the cylindrical tissue cores, the insertion of the tissue cores into the material blank, and the production of multi-blocks.
4. A double-melt procedure that is preferably used to create a firm bond between the cylindrical tissue cores and the material blank allows the production of a homogeneous, stable tissue block with multiple tissue samples, which can be further processed without technical or methodological limitations. The uniform, staggered heating of the material blank containing multiple inserted cylindrical tissue cores from below and above ensures both that the consistent orientation of the cylindrical tissue cores remains intact, and that the blank material melts homogeneously with the material in the cylindrical tissue cores, which gives the finished multi-block a high degree of stability. The method can be performed without extensive technical effort, and can therefore be used in any laboratory.

In summary, the invention presented here offers the opportunity to produce tissue blocks with multiple tissue samples as a service for other institutions, as well as to sell the technically simple method to other institutions, either as a complete unit (e.g. in the form of a modular system) or in parts (e.g. only material blanks).

One essential use of such multi-blocks is for the rapid and effective testing and characterization of monoclonal and polyclonal antibodies in regard to their specificity and sensitivity. The use of monoclonal and polyclonal antibodies is extremely important for diagnosis, characterization, stage classification, and therapy decisions in modern pathology, as well as for many scientific investigations. Prior to using a new antibody, however, one must test its specificity, i.e. its reaction pattern with normal and pathological tissue. This is normally done using immunohistochemical techniques. The corresponding antibody must also be tested with a number of normal and pathological tissue types. Such testing is very time-consuming, laborious, and costly, and can be significantly shortened by the use of multi-blocks. This procedure is naturally transferable to all testing techniques in addition to immunohistochemistry that are based on paraffin material, e.g. histochemical and biochemical stain reactions, and various hybridization techniques (in situ, fluorescence in situ hybridization (Fish), in situ PCR, in situ methylation PCR). The use of multi-blocks leads primarily to savings in time and costs in all of these laboratory techniques, and creates identical laboratory conditions, which also permits the acceleration of scientific investigations. Scientific studies with large patient populations can also be conducted and analyzed more quickly and cost-effectively.

The method described is not limited to the testing of human tissue. Animal and plant tissues can also be tested more quickly and cost-effectively, as can microorganisms, cultured cells, and matrix macromolecules.

A further advantage of this technique that is becoming increasingly important is improved quality control and simultaneous quality assurance, which is inherent in this method. Because all of the samples can be tested simultaneously under identical laboratory and testing conditions, false-positive and false-negative results can be detected quickly. Above all, the use of precisely characterized cell cultures in the form of multi-blocks with multiple, differing cell cultures can contribute materially to quality assurance and possibly also to the quantification of results in immunohistochemistry, which has since become a routine diagnostic method.

In summary, the present invention offers a method for the simple, quick, flexible, cost-effective, and reliable production of tissue blocks with multiple tissue samples, which permits simultaneous testing of multiple different human, animal, or plant tissues, as well as microorganisms or cell cultures, using all known testing techniques established for paraffin-embedded tissues, without technical or methodological supplements or limitations.

Figures 6A, 6B:
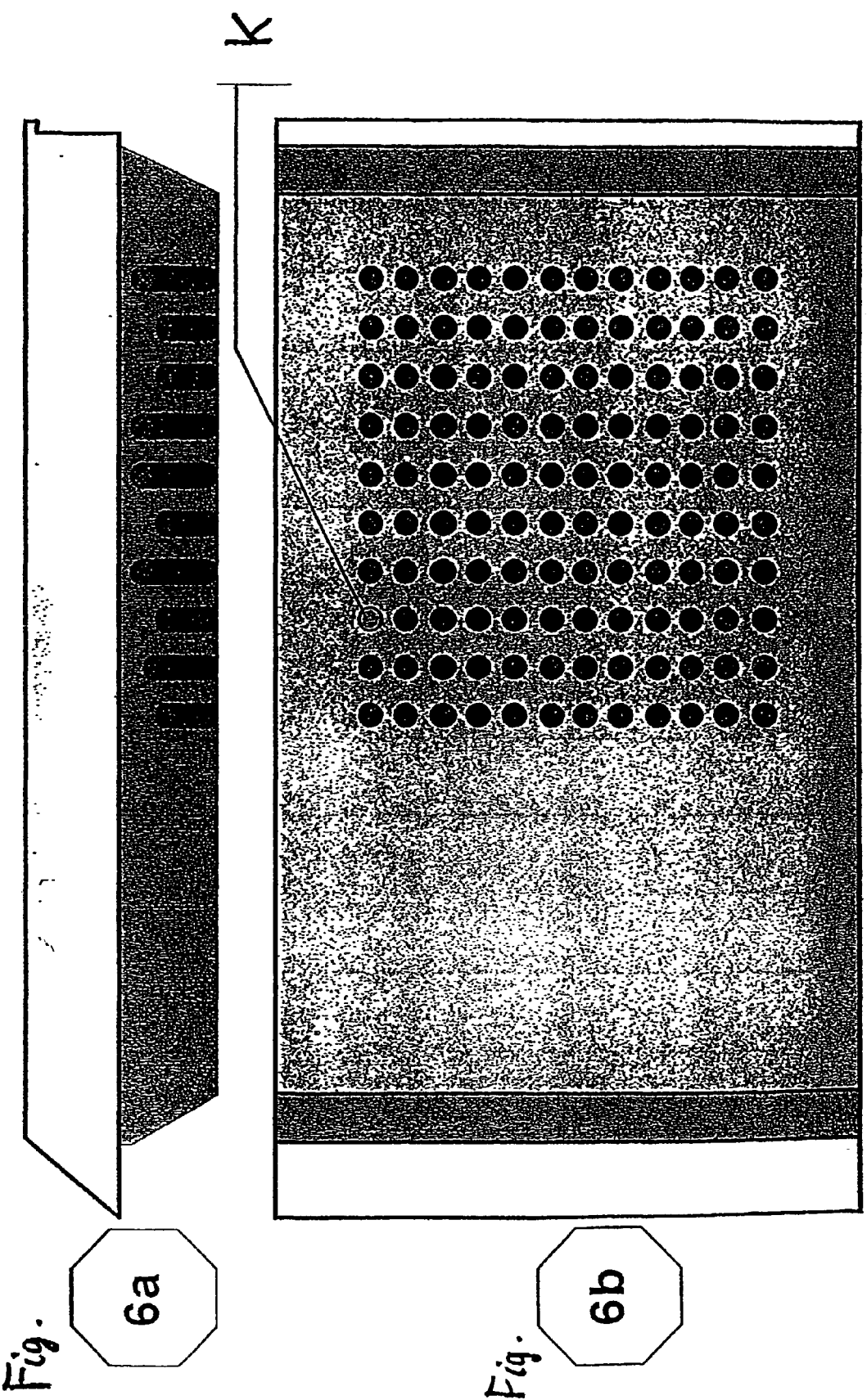

One single embodiment of the present invention is explained in greater detail below on the basis of the drawings. These drawings show the following:

FIG. 1a-c the individual parts of a casting mold for the material blank;

FIG. 2a,b the production of a material blank using the casting mold;

FIG. 3a, b the insertion of tissue samples into the material blank;

FIG. 4a, b the firm bonding of tissue samples with the material blank by means of temperature treatment steps;

FIG. 5a-c the placement of an embedding cassette on the material block and subsequent filling of the embedding cassette with additional hardenable material, and subsequent removal of an embedding tray;

FIG. 6a, b the finished material block retained by the embedding cassette, in a side view and a top view, with a tissue sample for purposes of orientation.

The basis for the production of multi-blocks is the production of a material blank, particularly a paraffin blank, in which the tissue samples, particularly cylindrical tissue cores, can later be inserted. This paraffin blank has dimensions of approximately 40×25 mm, and is therefore compatible with traditional paraffin blocks. The finished multi-block can therefore be cut and further processed in routine laboratories without special equipment or techniques.

The paraffin blanks are produced in a special casting mold using a direct casting technique. The composition of the casting mold is shown in FIG. 1a-c, with the finished casting mold shown in FIG. 1c. The casting mold consists e.g. of one aluminum block B, into which for example between 60 and 120 cylinder pins A (peg-shaped elements) with a diameter of e.g. 1.5 mm (DIN7) have been driven using pre-drilled holes. The cylinder pins are arranged parallel to one another and are firmly seated in the aluminum block. The aluminum block has an edge length of e.g. 40×28 mm and a height of 11 mm. Ninety-six holes, for example, with a diameter of 1.5 mm are drilled into this block. Ninety-six specially hardened cylinder pins with a diameter of 1.5 mm and a length of 20 mm are driven flush into all 96 holes. FIG. 1a shows a corresponding intermediate product in cross-section through one level of a row of pins.

A further embodiment of the casting mold consists of an aluminum plate into which any number of holes have been bored and cylinder pins driven in the manner described above. Instead of the pre-drilled embedding tray, a plate made of V2A steel that is e.g. 2–5 mm thick, with precisely fitting holes of e.g. 1.6 mm diameter, and which is raised e.g. 5 mm higher on its edge, is placed on the aluminum plate. This arrangement can be used to produce a multiple blank from which pieces with the necessary number of holes can be separated and further processed as single blanks.

Pursuant to FIG. 1b, an embedding tray C, similar to those typically used in a histological laboratory for pouring out paraffin from tissue blocks, has been modified with corresponding boreholes in such a way that it can be set directly on the aluminum block over the cylinder pins of the casting mold, and lies upon the block in such a way that it makes full contact (see FIG. 1c). For example, one can use a commercially available embedding tray with dimensions of 37×24×5 mm, which has been modified with holes drilled into the center of the indentation. In this way, e.g. 96 holes with diameters of 1.6 mm have been drilled into a regular 8×12 arrangement. The distance between the hole midpoints of a row is 1.9 mm, so that all of the boreholes result in a field of 14.9×22.5 mm.

Casting molds can also be similarly used with other quantities of holes and cylinder pins, e.g. 60 in a 6×10 arrangement or 24 in a 4×6 arrangement. The diameter of the cylinder pins and the holes in the modified embedding tray can also be varied.

According to FIG. 1c, the modified embedding tray is placed onto the aluminum block in such a way that the convex side of the modified embedding tray lies flat on the aluminum block. The cylinder pins extending through the tray thus project vertically on its concave side.

FIG. 2a, b describes how the material blank is produced. To accomplish this, the casting mold of FIG. 1c is reheated to approximately 65° on an adjustable hot plate. In this arrangement, approximately 3.5 ml of paraffin D heated to 70° is poured into the modified embedding tray so that it also flows between the cylinder pins. Here it is necessary either to have a sufficient initial temperature or else to slightly preheat the cylinder pins so that the paraffin does not cool off and therefore harden too rapidly. The blank E1 is then solidified by means of slow cooling at room temperature.

Once the paraffin blank E2 is completely hardened, the aluminum block B is reheated carefully and slightly (<40° C., so that the melting point of 56° C. for commercially available paraffin is not exceeded) in order to ease the removal of the modified embedding tray C together with the paraffin blank E2. As shown in FIG. 3a, the paraffin blank E2 is freed from the modified embedding tray by means of subsequent cooling (4° C.) and careful tapping. The paraffin blanks produced in this way can be stored at room temperature for an unlimited period of time. They can therefore be produced in quantity and also shipped.

FIG. 3b shows how tissue samples, particularly cylindrical tissue cores F, are inserted into the paraffin blank, with the blank being placed into a conventional embedding tray G for better handling. This also ensures that no cylindrical tissue cores can fall through and be lost when being inserted into the paraffin blank from above. Cylindrical tissue cores with a diameter of 1.5 mm and a length of 3–8 mm are inserted into the cavities in the paraffin blank that were preformed in the manner described above, and are then melted into a uniform multi-block. A core needle and a precisely fitted plunger are needed to produce these cylindrical tissue cores. The core needle and the plunger are produced from traditional biopsy needles, such as those used to obtain clinical tissue biopsies. The biopsy needle is shortened, the end is ground flat, and the outer edge of the core needle is ground smooth. Cylinders with a length of 3–8 mm are manually punched out of the paraffin blocks using the core needle produced in this manner, and the cylindrical tissue core is pushed out of the core needle with the plunger. All test objects embedded in paraffin can be punched out, e.g. tissue, embedded cells of human, animal, or plant origin, microorganisms, virus-infected cells, matrix macromolecules and other particles, etc. The cylindrical cores can be stored for an unlimited period of time, e.g. in Eppendorf reaction vessels, which enables the creation of libraries of punched samples, and obviates the need to store all of the tissue blocks at the same time.

FIG. 3b shows how 96 different cylindrical tissue cores F, as well as a paraffin blank as specified above, are produced for a multi-block. A conventional embedding tray G without modifications, i.e. without holes, is also required.

In this process, the paraffin blank is fitted precisely into a conventional embedding tray G, and at least some of the openings are filled with cylindrical tissue cores F. In this operation, attention should be paid to inserting the cylindrical tissue core into the paraffin blank with the smooth side, i.e. the cut surface, of the original paraffin block in front, so that the tissue being tested is directly cut into in the finished multi-block as well. A cylindrical tissue core consisting of a type of tissue that is completely foreign to the tissue being tested is inserted in an eccentric position (e.g. in the first row, third cavity from the right in a 96-hole block), in order to permit easy orientation of the section on the slide. Once all of the cavities in the paraffin blank are filled with cylindrical tissue cores, the blank with the cylindrical tissue cores is melted into a uniform paraffin block, which does not differ in its technical properties from a paraffin block containing only one tissue sample.

This melting procedure is presented in FIG. 4a, b. Preferably the embedding tray G with the paraffin blanks filled with cylindrical tissue cores is melted into a homogeneous paraffin block by means of a double-melt procedure. An essential element in this operation is that the double-melt procedure must retain the original geometry of the blocks, i.e. the cylindrical tissue cores must not fall over or otherwise change their original position during the melting operation, as this would make it impossible to assign the tissue samples in the section. The filled paraffin block in the conventional embedding tray is placed on an adjustable heating plate, such as a thermoplate or the block of a PCR machine. The double-melt procedure begins with slow heating from below until more than 50% of the thickness of the paraffin block (although not more than 80%) has liquefied (H1). Preferably the filled paraffin blank is preheated for 10–20 minutes to 40° C. A pulse of 70° C. (maximum 80° C.) heat lasting one minute or longer, essentially depending upon the heat output of the equipment used, is applied until the lower 2 to 3 mm (>50%<80%) of the blank/cylindrical core ensemble is melted through, without melting the entire block completely. The multi-block is then quickly cooled to 20° C. and stored on a material with good heat-conduction properties (copper plate, heating block, or PCR machine). The slow heating ensures that the paraffin in the cylindrical tissue cores also liquefies, and thus creates a close bond between the paraffin of the cylindrical tissue cores and the lower portion of the paraffin blank when it re-cools. This step, together with the second melting operation with overhead heat, described below, is decisive for the production of a homogeneous multi-block that can ultimately be further processed just as any normal standard paraffin block.

Following complete cooling, the second portion of the double-melt procedure presented in FIG. 4d takes place, in which a heat-caused liquefaction occurs similarly to the previously described procedure by means of overhead heat (H2), although in this case the upper portion of the paraffin blank with inserted cylindrical tissue cores is heated. In this procedure, the multi-block is irradiated from above with the help of an additional heat source (preferably an infrared heating lamp) until the multi-block is melted from above, although again without completely melting the multi-block. One prerequisite for this step is good heat elimination in the lower portion of the block.

A commercially available embedding cassette made of plastic (I), as normally used in the daily routine for producing paraffin blocks, is placed onto the liquefied surface of the paraffin according to FIG. 5a. Pre-heated paraffin (D), e.g. at 65° C., is now once again added until the remaining cavities are completely filled with paraffin, and the paraffin also completely covers the base of the embedding cassette I. The multi-block produced in this way is subsequently cooled off to room temperature (approximately 4 hours), and then the firmly cast-in embedding cassette is released from the embedding tray by tapping, as shown in FIG. 5c.

A finished paraffin block is shown in FIG. 6a, b in a side view and a bottom view, with K designating a tissue sample of a foreign tissue or plastic for orientation purposes. Tissue sections can be cut from such a paraffin block using known methods, e.g. a microtome or similar equipment, by cutting sections from the lower main surface of the block, preparing them for microscopy in a thickness of 2–5 μm, and mounting them on a slide, such as a glass slide. In order to ensure a clear orientation of all of the cylindrical tissue cores inserted into the multi-block, one of the cylindrical tissue cores consists of a foreign tissue or easily cut plastic (K). This marking cylinder must be placed in an asymmetric position so as to maintain clear, positive identification and orientation on a slide, even when it is rotated or mounted in a mirror-image (i.e. from the reverse side).

The sequential double-melt of the multi-block from two sides as described above, while preventing the complete melting of the block, guarantees a consistent arrangement of the cylindrical tissue cores in the multi-block. All areas of the block, however, are completely melted in sequence. This procedure allows the tissue samples to closely bond with the surrounding paraffin in the new multi-block, and thus prevents individual cylinder disks from falling out or "dispersing" on the water bath when tissue sections are being produced. Because this block can no longer be technically distinguished from paraffin blocks containing only one tissue sample, it can be further processed in the same manner as these other blocks without the need for special equipment.

The described method can be changed and modified in many ways. For example, instead of paraffin, the material blank can be produced using another material that is also suitable, free-flowing, and capable of hardening, such as a suitable epoxy resin or other similar material. It can also be designed in such a way that the openings in the material blank provided for insertion of the tissue samples do not completely penetrate the block, but instead end at a specific depth in the material blank, for which another casting mold must be used. This means that after the material block with the multiple tissue samples is produced, a certain thickness must be removed before tissue sections with multiple tissue samples can be cut off of the block.

The invention claimed is:

1. A method for the production of a material block having one or more embedded test samples, the method comprising:
   a. casting a material blank from a mold, the material blank having one or more openings to accommodate cylinders of material, the one or more openings extending into the material blank from a first surface of the material blank in the direction of a second surface of the material blank;
   b. inserting at least one cylinder of material in at least one of the one or more openings of said material blank, the at least one cylinder with or without an embedded test object in an embedding material, wherein said embedding material is the same material as a material of the material blank; and
   c. bonding the at least one cylinder of material to the material of the material blank so as to affix the cylinders into the material blank;
      wherein bonding the at least one cylinder of material to the material of the material blank includes at least one melting procedure; and
      wherein bonding the at least one cylinder of material to the material of the material blank includes a double melt procedure, whereby heat is applied to the first surface of the material blank during a first step of the double-melt procedure, and heat is applied to the second surface of the material blank during a second step of the double-melt procedure.

2. The method according to claim 1, wherein the one or more openings penetrate through the material blank.

3. The method according to claim 2, wherein the mold comprises a substrate having a substrate surface from which one or more peg-shaped elements projects, the one or more peg-shaped elements corresponding to the one or more openings in the material blank, and wherein casting the material blank comprises:
   a. pouring the material of the material blank onto the substrate surface; and
   b. removing the material blank from the substrate after the material blank has hardened.

4. The method according to claim 3, wherein the substrate is made of aluminum.

5. The method according to claim 3, wherein the casting the material blank further comprises:
   a. prior to pouring the material of the material blank, placing a first tray onto the substrate surface, the first tray having a top surface and a bottom surface, the first tray having holes on the top surface that extend through to the bottom surface that correspond to the one or more peg-shaped elements, wherein the one or more peg-shaped elements protrude through the holes, and the bottom surface of the first tray lies upon and contacts the substrate surface;
   b. once the material blank has hardened, lifting the first tray together with the material blank from the casting mold; and
   c. removing the material blank.

6. The method according to claim 1, wherein the one or more cylinders of material are rod or cylinder-shaped, and are obtained by being punched out of sample blocks in which the test objects are embedded in the embedding material.

7. The method according to claim 6, wherein the embedding material is paraffin.

8. The method according to claim 1, wherein the one or more openings on the first surface penetrate through the material blank to form openings on the second surface, and the method further comprises:
   a. prior to inserting the at least one cylinder of material, placing the material blank into a second tray, so that one of the first surface and the second surface contacts a surface of the second tray, and
   b. inserting the at least one cylinder of material through the one or more openings until the at least one cylinder of material contacts the surface of the second tray.

9. The method according to claim 8, further comprising:
   a. affixing an embedding cassette to the material block; and
   b. pouring a moldable material into the embedding cassette.

10. The method according to claim 1, further comprising inserting a marking cylinder for orientation purposes.

11. The method according to claim 10, wherein the marking cylinder comprises a tissue that is different from the test object and a plastic.

12. The method according to claim 1, wherein bonding the at least one cylinder of material to surrounding material of the material blank includes melting the at least one cylinder of material to the material blank.

13. The method according to claim 1, further comprising:
   a. affixing an embedding cassette to the material block so that a base of the embedding cassette maintains a distance from a surface of the material blank from which the cylinders of material were inserted; and
   b. pouring a moldable material into the embedding cassette.

14. The method according to claim 13, wherein pouring the moldable material into the embedding cassette includes pouring the moldable material until remaining cavities in the material block are completely filled with the material.

15. The method according to claim 13, wherein pouring the moldable material into the embedding cassette includes pouring the moldable material until the moldable material covers the base of the embedding cassette.

16. A method according to claim 1, wherein the material blank is made of paraffin.

17. A method for the production of a material block having a number of test samples, the method comprising:
   a. casting a material blank from a mold, such that the material blank has one or more openings for accommodating cylinders of material, the one or more openings extending into the blank from first surface of the material blank in the direction of a second surface of the material blank;
   b. inserting at least one cylinder of material in at least one of the one or more openings; and
   c. bonding the at least one cylinder of material to surrounding material of the material blank to affix the cylinders into the material blank
      wherein, bonding the at least one cylinder of material to surrounding material of the material blank includes at least one melting procedure;
      wherein, bonding the at least one cylinder of material to surrounding material of the material blank includes melting the at least one cylinder of material to the material blank; and
      wherein bonding the at least one cylinder of material to surrounding material of the material blank includes a double-melt procedure, whereby heat is applied to the initial first surface of the material blank during a first step of the double-melt procedure, and heat is applied to the second surface of the material blank during a second step of the double-melt procedure.

* * * * *